(12) United States Patent
Yoshizawa et al.

(10) Patent No.: US 10,398,728 B2
(45) Date of Patent: Sep. 3, 2019

(54) JELLY-LIKE MEDICINAL COMPOSITION OF POTASSIUM IODIDE

(71) Applicant: Nichi-Iko Pharmaceutical Co., Ltd., Toyama-shi, Toyama (JP)

(72) Inventors: Naoko Yoshizawa, Namerikawa (JP); Sho Suzuki, Toyama (JP)

(73) Assignee: Nichi-Iko Pharmaceutical Co., Ltd. (JP)

( * ) Notice: Subject to any disclaimer, the term of this patent is extended or adjusted under 35 U.S.C. 154(b) by 0 days.

(21) Appl. No.: 15/354,425

(22) Filed: Nov. 17, 2016

(65) Prior Publication Data

US 2017/0065633 A1   Mar. 9, 2017

Related U.S. Application Data

(63) Continuation of application No. PCT/JP2015/053536, filed on Feb. 9, 2015.

(30) Foreign Application Priority Data

Aug. 8, 2014  (JP) ................................ 2014-163146

(51) Int. Cl.
| | |
|---|---|
| A61K 33/18 | (2006.01) |
| A61K 47/10 | (2017.01) |
| A61K 9/06 | (2006.01) |
| A61K 47/32 | (2006.01) |
| A61K 9/00 | (2006.01) |
| A61K 47/36 | (2006.01) |

(52) U.S. Cl.
CPC ............ *A61K 33/18* (2013.01); *A61K 9/0056* (2013.01); *A61K 9/06* (2013.01); *A61K 47/10* (2013.01); *A61K 47/32* (2013.01); *A61K 47/36* (2013.01)

(58) Field of Classification Search
None
See application file for complete search history.

(56) References Cited

U.S. PATENT DOCUMENTS

| | | |
|---|---|---|
| 5,932,235 A | 8/1999 | Ninomiya et al. |
| 7,014,871 B1 | 3/2006 | Parsons et al. |
| 2005/0181025 A1 | 8/2005 | Velebny et al. |

FOREIGN PATENT DOCUMENTS

| | | | |
|---|---|---|---|
| JP | 09-187233 A | | 7/1997 |
| JP | 09-194346 A | | 7/1997 |
| JP | 2002-104974 A | | 4/2002 |
| JP | 2002104974 A | * | 4/2002 |
| JP | 2002-539140 A | | 11/2002 |
| JP | 2004099559 A | * | 4/2004 |
| JP | 2005-514445 A | | 5/2005 |
| JP | 3665498 B2 | | 6/2005 |
| JP | 2010-265209 A | | 11/2010 |

OTHER PUBLICATIONS

English Translation of JP2002104974 retrieved from JPLAT-PAT on Sep. 27, 2017.*
English translation of Abstract of JP2004099559A retrieved from SciFinder on Apr. 18, 2018.*
English Translation of JP2004099559A retrieved from Espacenet on Apr. 18, 2018.*
English translation of JP2000256181 retrieved from Espacenet on Aug. 22, 2018.*
Genshiryoku Saigaiji ni Okeru Antei Yosozai Yobo Fukuyo no Kangaekata ni Tsuite, Nuclear Safety Commission of Japan Genshiryoku Shisetsu-to Bosai Senmon Bukai, pp. 14-16, http://www.u-tokyo-rad.jp/data/ninpuyouso.pdf (Apr. 2002).
Atsuko Fukui, "Shoni ni Motornerareru Kusuri no Katachi Jelly Seizai no Shoni eno Tekiyo", Journal of Practical Pharmacy, vol. 64, No. 10, pp. 2633-2639 (Sep. 5, 2013).

* cited by examiner

*Primary Examiner* — Jessica Worsham

(74) *Attorney, Agent, or Firm* — Harness, Dickey & Pierce, P.L.C.

(57) ABSTRACT

A jelly-like potassium iodide pharmaceutical composition exhibits excellent storage stability and excellent dissolution properties, and can be taken easily. The jelly-like potassium iodide pharmaceutical composition includes potassium iodide as an active ingredient, a gelling agent, and a dispersion medium.

5 Claims, 4 Drawing Sheets

FIG. 1

16.3 mg JELLY ACCELERATED STABILITY
TEST RESULTS (40°C, 75%RH)

[QUANTITATIVE TEST] (n=3)

| MEASUREMENT TIME | LOT NO. | 24A1 | 24B1 | 24C1 |
|---|---|---|---|---|
| INITIAL VALUE | AVERAGE VALUE | 100.2 | 100.3 | 100.3 |
| | RESIDUAL RATE | — | — | — |
| 1 MONTH | AVERAGE VALUE | 99.7 | 99.6 | 99.6 |
| | RESIDUAL RATE | 99.5 | 99.3 | 99.3 |
| 3 MONTHS | AVERAGE VALUE | 99.7 | 99.8 | 99.4 |
| | RESIDUAL RATE | 99.5 | 99.5 | 99.1 |
| 6 MONTHS | AVERAGE VALUE | 100.6 | 100.9 | 100.5 |
| | RESIDUAL RATE | 100.4 | 100.6 | 100.2 |

FIG. 2

16.3 mg JELLY ACCELERATED STABILITY
TEST RESULTS (40°C, 75%RH)

[DISSOLUTION TEST] (n=3)

| MEASUREMENT TIME | LOT NO. | 24A1 | 24B1 | 24C1 |
|---|---|---|---|---|
| INITIAL VALUE | AVERAGE VALUE | 98.7 | 99.6 | 99.1 |
| 1 MONTH | AVERAGE VALUE | 98.4 | 100.5 | 99.8 |
| 3 MONTHS | AVERAGE VALUE | 99.5 | 100.6 | 100.6 |
| 6 MONTHS | AVERAGE VALUE | 100.3 | 102.0 | 100.4 |

FIG. 3

16.3 mg JELLY ACCELERATED STABILITY
TEST RESULTS (40°C, 75%RH)

[PURITY TEST (RELATED SUBSTANCES)]   (n=3)

| MEASUREMENT TIME / LOT NO. | | 24A1 | 24B1 | 24C1 |
|---|---|---|---|---|
| INITIAL VALUE | AVERAGE | 0.09 | 0.12 | 0.05 |
| 1 MONTH | AVERAGE | 0.10 | 0.13 | 0.10 |
| 3 MONTHS | AVERAGE | 0.11 | 0.18 | 0.11 |
| 6 MONTHS | AVERAGE | 0.15 | 0.23 | 0.11 |

FIG. 4

32.5 mg JELLY ACCELERATED STABILITY
TEST RESULTS (40°C, 75%RH)

[QUANTITATIVE TEST]   (n=3)

| MEASUREMENT TIME / LOT NO. | | 24A1 | 24B1 | 24C1 |
|---|---|---|---|---|
| INITIAL VALUE | AVERAGE VALUE | 100.1 | 100.1 | 100.1 |
| | RESIDUAL RATE | — | — | — |
| 1 MONTH | AVERAGE VALUE | 99.9 | 99.5 | 100.0 |
| | RESIDUAL RATE | 99.8 | 99.4 | 99.4 |
| 3 MONTHS | AVERAGE VALUE | 99.3 | 99.5 | 99.7 |
| | RESIDUAL RATE | 99.2 | 99.4 | 99.4 |
| 6 MONTHS | AVERAGE VALUE | 100.5 | 100.3 | 100.5 |
| | RESIDUAL RATE | 100.4 | 100.2 | 100.2 |

FIG. 5

32.5 mg JELLY ACCELERATED STABILITY
TEST RESULTS (40°C, 75%RH)

[DISSOLUTION TEST] (n=3)

| MEASUREMENT TIME | LOT NO. | 24A1 | 24B1 | 24C1 |
|---|---|---|---|---|
| INITIAL VALUE | AVERAGE VALUE | 100.8 | 99.4 | 98.4 |
| 1 MONTH | AVERAGE VALUE | 101.6 | 100.3 | 100.8 |
| 3 MONTHS | AVERAGE VALUE | 101.5 | 100.0 | 99.8 |
| 6 MONTHS | AVERAGE VALUE | 104.1 | 102.0 | 102.3 |

FIG. 6

32.5 mg JELLY ACCELERATED STABILITY
TEST RESULTS (40°C, 75%RH)

[PURITY TEST (RELATED SUBSTANCES)] (n=3)

| MEASUREMENT TIME | LOT NO. | 24A1 | 24B1 | 24C1 |
|---|---|---|---|---|
| INITIAL VALUE | AVERAGE | 0.08 | 0.08 | 0.09 |
| 1 MONTH | AVERAGE | 0.09 | 0.10 | 0.07 |
| 3 MONTHS | AVERAGE | 0.14 | 0.10 | 0.12 |
| 6 MONTHS | AVERAGE | 0.12 | 0.14 | 0.13 |

DISSOLUTION BEHAVIOR OF 32.5 mg PREPARATION

[RESPONDENTS]
FOUR MEN (20 TO 29 YEARS OLD: 1, 30 TO 39 YEARS OLD: 2, 50 TO 59 YEARS OLD: 1)
FOUR WOMEN (20 TO 29 YEARS OLD: 2, 30 TO 39 YEARS OLD: 1, 40 TO 49 YEARS OLD: 1)

JELLY-LIKE MEDICINAL COMPOSITION OF POTASSIUM IODIDE

CROSS REFERENCE TO RELATED APPLICATION

This application is a continuation of International Patent Application No. PCT/JP2015/053536, having an international filing date of Feb. 9, 2015, which designated the United States, the entirety of which is incorporated herein by reference. Japanese Patent Application No. 2014-163146 filed on Aug. 8, 2014 is also incorporated herein by reference in its entirety.

TECHNICAL FIELD

The present invention relates to an iodine preparation (formulation). In particular, the invention relates to a jelly-like pharmaceutical composition.

BACKGROUND ART

A potassium iodide pill and a potassium iodide powder (bulk powder) have been provided as iodine preparations.

These iodine preparations are used for the treatment of thyroid tumor that is accompanied by hyperthyroidism, the treatment of difficulty in sputum and expectoration due to bronchitis and asthma, the treatment of tertiary syphilis, and radioiodine ($^{131}$I) thyroid therapy.

It has been pointed out that, when radioiodine has been released due to a nuclear disaster, the radioiodine may selectively accumulate in the thyroid, and thyroid cancer and the like may occur through internal exposure.

Such internal exposure may be prevented by administration of a stable iodine preparation.

A potassium iodide pill that is currently marketed as a stable iodine preparation contains 50 mg of potassium iodide.

According to "Preventive Administration of Stable Iodine Preparation in case of Nuclear Disaster" published by the Nuclear Safety Commission in April 2002, it is recommended that the dose of a stable iodine preparation be 16.3 mg when administered to a newborn baby, and be 32.5 mg when administered to a 1-month-old to 3-year-old infant. "Guidelines for Administration of Stable Iodine Preparation in case of Nuclear Disaster" published by the Japan Medical Association in March, 2014 also recommend the above doses.

Therefore, when the dose of a stable iodine preparation is less than 50 mg (e.g., when a stable iodine preparation is orally administered to an infant below the age of 3), it is necessary to pulverize a pill, and administer a given amount of preparation.

In particular, it is recommended to dissolve a potassium iodide bulk powder in water, and add a proper quantity of the solution to simple syrup when administering a stable iodine preparation to a newborn baby or an infant. However, it is very difficult to take such measures in case of emergency.

Since potassium iodide tastes bitter, it is necessary to improve ease of intake in view of administration to a child (particularly a newborn baby and an infant).

JP-A-2010-265209 discloses a liquid iodine preparation. However, the liquid iodine preparation disclosed in JP-A-2010-265209 has a problem with regard to ease of intake.

When a stable iodine preparation is used to prevent internal exposure, it is necessary to distribute a stable iodine preparation in advance. Therefore, it is necessary to provide a stable iodine preparation that can be stored for a certain period.

Accordingly, development of a stable iodine preparation that can be taken easily and stored for a certain period has been desired.

SUMMARY OF INVENTION

Technical Problem

An object of the invention is to provide a jelly-like potassium iodide pharmaceutical composition that exhibits excellent storage stability and excellent dissolution properties, and can be taken easily.

Solution to Problem

A jelly-like pharmaceutical composition according to the invention comprises potassium iodide as an active ingredient, a gelling agent, and a dispersion medium.

A carrageenan, xanthan gum, carob bean gum, pectin, gellan gum, acacia gum, agar, gelatin, konjac, and the like may be used either alone or in combination as the gelling agent used in connection with the invention.

Carrageenans are one type of linear sulfur-containing polysaccharide, and are classified into κ-carrageenan, ι-carrageenan, and λ-carrageenan.

Carob bean gum has compatibility with a carrageenan and xanthan gum, and may be used in combination therewith.

Carob bean gum is also referred to as locust bean gum, and includes a galactomannan as the main component.

The jelly-like pharmaceutical composition may include a stabilizer. Polyacrylic acid, partially neutralized polyacrylic acid, or a polyacrylic acid salt may be used as the stabilizer.

Sodium polyacrylate is preferable as the polyacrylic acid salt.

A mixture that includes water and a polyhydric alcohol is preferable as the dispersion medium used in connection with the invention. Examples of the polyhydric alcohol include glycerol, propylene glycol, and the like.

The jelly-like pharmaceutical composition according to the invention may include at least one of a sweetener, a buffer, a preservative, and a flavor.

Since potassium iodide tastes bitter, it is preferable to add a sweetener to the jelly-like pharmaceutical composition when the jelly-like pharmaceutical composition is intended for newborn babies and infants, for example.

Examples of the sweetener include D-sorbitol, D-mannitol, sodium saccharin, purified sucrose, and the like.

Examples of the buffer include citric acid, sodium citrate, dipotassium phosphate, sodium phosphate, and the like.

Examples of the preservative include propylparaben, ethylparaben, methylparaben, and the like.

The term "flavor" used herein refers to a natural flavor, a synthetic flavor, and a flavoring agent that includes either or both of a natural flavor and a synthetic flavor. Examples of the flavor include fruit juice, essential oil, menthol, and the like.

The jelly-like pharmaceutical composition according to the invention may be provided in a state in which a given oral dose of the jelly-like pharmaceutical composition is contained in a stick-like package.

In this case, the stick-like package may be designed so that about half of the stick-like package is filled with clean air, and the jelly-like pharmaceutical composition (jelly) is discharged when the air-containing part of the stick-like package is pressed (i.e., air push-type jelly package).

For example, technology disclosed in Japanese Patent No. 3665498 may be employed.

Advantageous Effects of Invention

The jelly-like potassium iodide pharmaceutical composition according to the invention includes potassium iodide as an active ingredient in the jelly, and allows a parent and the like to easily administer the jelly-like pharmaceutical composition to a newborn baby or an infant.

BRIEF DESCRIPTION OF DRAWINGS

FIG. 1 illustrates quantitative test results (16.3 mg preparation).
FIG. 2 illustrates dissolution test results (16.3 mg preparation).
FIG. 3 illustrates purity test results (16.3 mg preparation).
FIG. 4 illustrates quantitative test results (32.5 mg preparation).
FIG. 5 illustrates dissolution test results (32.5 mg preparation).
FIG. 6 illustrates purity test results (32.5 mg preparation).

DESCRIPTION OF EMBODIMENTS

Figure 7:
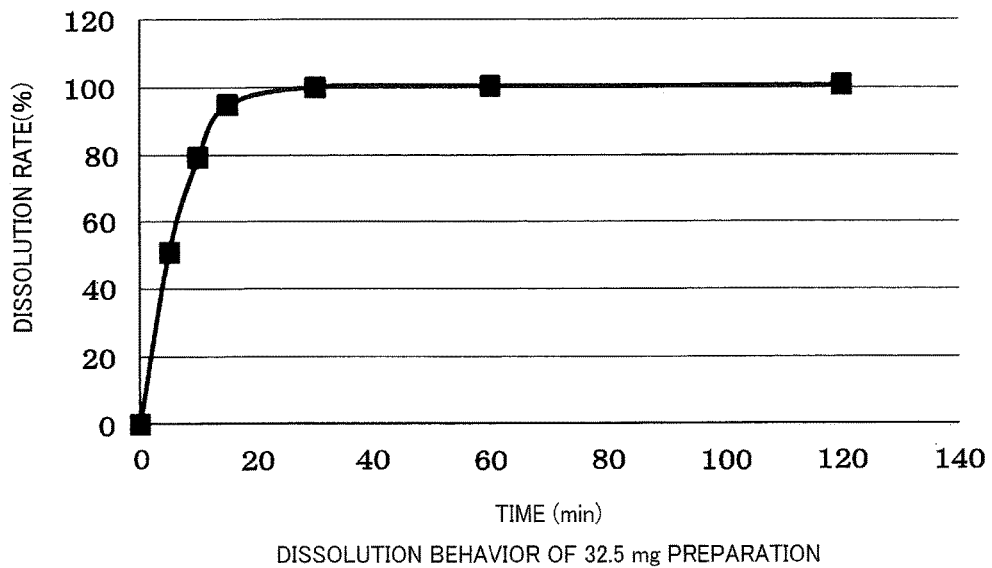
FIG. 7 illustrates dissolution behavior test results (32.5 mg preparation).

Examples of the formulation of the jelly-like potassium iodide pharmaceutical composition according to the invention are listed in Table 1.

Note that the jelly-like potassium iodide pharmaceutical composition (jelly-like pharmaceutical composition) according to the invention is not limited thereto.

TABLE 1

| Component | 16.3 mg preparation | | 32.5 mg preparation | |
| --- | --- | --- | --- | --- |
| | Amount (mg) | (%) | Amount (mg) | (%) |
| Potassium iodide | 16.3 | 1.63 | 32.5 | 1.625 |
| ι-Carrageenan | 5 | 0.5 | 10 | 0.5 |
| κ-Carrageenan | 1.1 | 0.11 | 2.2 | 0.11 |
| Carob bean gum | 1.9 | 0.19 | 3.8 | 0.19 |
| Sodium polyacrylate | 0.03 | 0.003 | 0.06 | 0.003 |
| Glycerol | 100 | 10 | 200 | 10 |
| D-Sorbitol | 200 | 20 | 400 | 20 |
| Sodium saccharin | 2 | 0.2 | 4 | 0.2 |
| Sodium citrate hydrate | 5 | 0.5 | 10 | 0.5 |
| Citric acid hydrate | 0.3 | 0.03 | 0.6 | 0.03 |
| Propylparaben | 0.15 | 0.015 | 0.3 | 0.015 |
| Flavor | 1 | 0.1 | 2 | 0.1 |
| Purified water | Proper quantity | 66.722 | Proper quantity | 66.727 |
| Total | 1,000 | 100 | 2,000 | 100 |

Production Example

The content (16.3 mg or 32.5 mg) of potassium iodide in the preparation (composition) was set in accordance with "Preventive Administration of Stable Iodine Preparation in case of Nuclear Disaster". The 16.3 mg preparation listed in Table 1 was produced as described below.

Note that the amount of each component mentioned below is based on 1 g of the preparation.

5 mg of sodium citrate hydrate, 0.3 mg of citric acid hydrate, 2 mg of sodium saccharin, and 100 mg of glycerol were added to a proper quantity of purified water, and the mixture was stirred and heated to obtain a solution. 5 mg of ι-carrageenan, 1.1 mg of κ-carrageenan, 1.9 mg of carob bean gum, 0.03 mg of sodium polyacrylate, and 0.15 mg of propylparaben were mixed with 200 mg of D-sorbitol, and the mixture was added to the solution, and the resulting mixture was stirred and heated to 80° C. to obtain a solution.

After the addition of a solution prepared by dissolving 16.3 mg of potassium iodide in purified water, the mixture was stirred.

After the addition of 1 mg of a strawberry flavor (flavor), the mixture was stirred.

After sterilizing the mixture at 80° C. for 1 hour, 1 g of the mixture was put in a stick-like container, and cooled to room temperature.

An accelerated stability test (40° C., 75% RH) was performed using the 16.3 mg preparation (contained in a stick-like container) produced as described above, and a 32.5 mg preparation (contained in a stick-like container) produced in the same manner as described above. The results are shown in FIGS. 1 to 6.

(1) A quantitative Test was Performed as Described Below.
Preparation of Sample Solution The preparation was accurately weighed in an amount equivalent to about 65 mg of potassium iodide. After the addition of 60 mL of water, the preparation was dispersed by heating in a water bath at about 80° C., and then cooled, followed by the addition of water to accurately adjust the amount of the mixture to 100 mL. 10 mL of the mixture was accurately pipetted. 10 mL of an internal standard solution (i.e., a solution of ethyl p-hydroxybenzoate in acetonitrile (3→1000)) was added, followed by the addition of water to adjust the amount of the mixture to 100 mL to obtain a sample solution.

Preparation of Standard Solution

Quantitative potassium iodide was dried at 105° C. for 4 hours, and about 65 mg of the potassium iodide was weighed, followed by the addition of water to accurately adjust the amount of the mixture to 100 mL. 10 mL of the mixture was accurately pipetted. 10 mL of an internal standard solution was added, followed by the addition of water to adjust the amount of the mixture to 100 mL to obtain a standard solution.

Measurement Method

5 μL of the sample solution and 5 μL of the standard solution were subjected to high-performance liquid chromatography under the following conditions, and the ratio of the peak area of iodide ions to the peak area of the internal standard was calculated to calculate the content (amount) of potassium iodide.

Measurement Conditions

Detector: UV absorptiometer (measurement wavelength: 225 nm)
Column: A column packed with octadecylsilylated silica gel for liquid chromatography was used.
Mobile phase: The mobile phase was prepared by adding 0.5 mL of a 0.5 mol/L tetrabutylammonium hydrogen phosphate solution and 300 mL of acetonitrile to 700 mL of water, and adjusting the pH of the mixture to 3.0 using phosphoric acid.

(2) A Dissolution Test was Performed as Described Below.
Test Conditions
900 mL of water was used as a test liquid, and the test was performed at 50 rpm in accordance with "Dissolution Test (Method 2)" specified by the Japanese Pharmacopoeia (see "General Tests").
Test Method
The preparation removed from the stick-like container was subjected to the dissolution test. When 30 minutes had elapsed, 20 mL or more of the eluate was removed, and filtered through a membrane filter having a pore size of 0.45 μm or less. After removing 10 mL of the filtrate, the subsequent filtrate was diluted with water so as to include about 18 μg/mL of potassium iodide to obtain a sample solution.
Preparation of Standard Solution
Quantitative potassium iodide was dried at 105° C. for 4 hours, and about 36 mg of the potassium iodide was weighed, followed by the addition of water to accurately adjust the amount of the mixture to 100 mL. 5 mL of the mixture was accurately weighed, and water was added to the mixture to adjust the amount of the mixture to 100 mL to obtain a standard solution.
Measurement Method
5 μL of the sample solution and 5 μL of the standard solution were subjected to high-performance liquid chromatography under the following conditions, and the peak area of iodide ions was calculated to calculate the content (amount) of potassium iodide.
Measurement Conditions
The same conditions as those employed for the quantitative test were used.
(3) A Purity Test was Performed as Described Below.
Preparation of Sample Solution
6 g of the jelly was weighed. After the addition of 8 mL of water, the jelly was dispersed by heating in a water bath at about 80° C. After cooling the dispersion, 11 mL of acetonitrile was added to the dispersion, and the mixture was centrifuged. 5 mL of the supernatant liquid was collected, followed by the addition of water to adjust the amount of the mixture to 25 mL to obtain a sample solution.
Preparation of Standard Solution
1 mL of the sample solution was accurately weighed, and water was added to the sample solution to accurately adjust the amount of the mixture to 200 mL to obtain a standard solution.
Measurement Method
5 μL of the sample solution and 5 μL of the standard solution were subjected to high-performance liquid chromatography under the following conditions, and the peak area of iodide ions in the standard solution and the peak area of impurities in the sample solution were calculated to calculate the content (amount) of impurities.
Measurement Conditions
Detector: UV absorptiometer (measurement wavelength: 210 nm)
Column: A column packed with octadecylsilylated silica gel for liquid chromatography was used.

Mobile phase A: A mobile phase A was prepared by adding 0.5 mL of a 0.5 mol/L tetrabutylammonium hydrogen phosphate solution and 300 mL of methanol to 700 mL of water, and adjusting the pH of the mixture to 2.8 using phosphoric acid.
Mobile phase B: A mobile phase B was prepared by adding 5 mL of a 0.5 mol/L tetrabutylammonium hydrogen phosphate solution and 500 mL of methanol to 500 mL of water, and adjusting the pH of the mixture to 2.8 using phosphoric acid.
Flowing of mobile phases: The mixing ratio of the mobile phase A to the mobile phase B was changed to control the concentration gradient.
It was confirmed from the test results that the jelly-like pharmaceutical composition according to the invention exhibits excellent storage stability.
FIG. 7 illustrates the dissolution behavior test results obtained using the 32.5 mg preparation.
(1) The Dissolution Behavior Test was Performed as Described Below.
Test Conditions
The dissolution behavior test was performed under the same conditions as those employed for the dissolution test.
Test Method
The preparation removed from the stick-like container was subjected to the dissolution behavior test. 10 mL of the eluate was collected at an appropriate timing, and water heated to 37±0.5° C. was added immediately. The collected eluate was filtered through a membrane filter having a pore size of 0.45 μm or less. After removing 3 mL of the filtrate, the subsequent filtrate was diluted with water so as to include about 18 μg/mL of potassium iodide to obtain a sample solution.
Preparation of Standard Solution
A standard solution was prepared in the same manner as described above in connection with the dissolution test.
Measurement Method
5 μL of the sample solution and 5 μL of the standard solution were subjected to high-performance liquid chromatography under the following conditions, and the peak area of iodide ions was calculated to calculate the content (amount) of potassium iodide.
Measurement Conditions
The same conditions as those employed for the quantitative test were used.
It was confirmed from the test results that the jelly-like pharmaceutical composition according to the invention exhibits excellent dissolution properties.
The effect of the mixing ratio of the gelling agent to D-sorbitol was also determined.
A preparation was produced in the same manner as described above using the formulation listed in Table 2, and the state of the resulting preparation was evaluated.
The total amount of each of Samples No. 1 to No. 7 was 1 g (16.3 mg preparation), and the total amount of each of Samples No. 8 to No. 10 was 2 g (32.5 mg preparation).

TABLE 2

| Component (%) | Sample | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Potassium iodide | 1.63 | 1.63 | 1.63 | 1.63 | 1.63 | 1.63 | 1.63 | 1.625 | 1.625 | 1.625 |
| ι-Carrageenan | 0.47 | 0.47 | 0.5 | 0.5 | 0.5 | 0.39 | 0.5 | 0.61 | 0 | 0 |

TABLE 2-continued

| Component (%) | Sample | | | | | | | | | |
|---|---|---|---|---|---|---|---|---|---|---|
| | 1 | 2 | 3 | 4 | 5 | 6 | 7 | 8 | 9 | 10 |
| κ-Carrageenan | 0.11 | 0.11 | 0.12 | 0.12 | 0.11 | 0.09 | 0.12 | 0 | 0.61 | 0.3 |
| Carob bean gum | 0.19 | 0.19 | 0.2 | 0.2 | 0.19 | 0.15 | 0.2 | 0.19 | 0.19 | 0.19 |
| Sodium polyacrylate | 0.003 | 0.003 | 0.003 | 0.003 | 0.003 | 0.003 | 0.003 | 0.003 | 0.003 | 0.003 |
| Glycerol | 10 | 10 | 10 | 10 | 10 | 10 | 10 | 10 | 10 | 10 |
| D-Sorbitol | 20 | 25 | 20 | 25 | 20 | 30 | 30 | 20 | 20 | 20 |
| Sodium citrate hydrate | 0.5 | 0.5 | 0.5 | 0.5 | 0.5 | 0.5 | 0.5 | 0.5 | 0.5 | 0.5 |
| Citric acid hydrate | 0.03 | 0.03 | 0.03 | 0.03 | 0.03 | 0.03 | 0.03 | 0.03 | 0.03 | 0.03 |
| Propylparaben | 0.015 | 0.015 | 0.015 | 0.015 | 0.015 | 0.015 | 0.015 | 0.015 | 0.015 | 0.015 |
| Purified water | Proper quantity | Proper quantity | Proper quantity | Proper quantity | Proper quantity | Proper quantity | Proper quantity | Proper quantity | Proper quantity | Proper quantity |
| Total | 100 | 100 | 100 | 100 | 100 | 100 | 100 | 100 | 100 | 100 |

Samples No. 1 to No. 10 listed in Table 2 were in the form of a jelly-like composition.

Whether or not the jelly-like composition (jelly) could be easily discharged using an air push-type stick-like package was also evaluated from the viewpoint of ease of intake.

In Sample No. 6 and Sample No. 7, the ratio (content) of D-sorbitol (sugar (sweetener)) was 30%. Sample No. 7 in which the ratio (content) of ι-carrageenan was 0.5%, and the ratio (content) of κ-carrageenan was 0.12% was in the form of jam-like jelly, and part of the preparation remained without being discharged when the preparation was discharged using an air push-type stick-like package.

Sample No. 6 in which the ratio (content) of D-sorbitol was 30% was in the form of a loose, but elastic jelly Therefore, the content of the sweetener (D-sorbitol) is preferably set to 30% or less, and more preferably 15 to 25%.

Sample No. 8 in which the ratio (content) of ι-carrageenan was 0.61% and the ratio (content) of κ-carrageenan was 0%, and Samples No. 9 and No. 10 in which the ratio (content) of ι-carrageenan was 0% and the ratio (content) of κ-carrageenan was 0.61% or 0.3%, were in the form of jelly. Note that Sample No. 8 had very high viscosity. Samples No. 9 and No. 10 could be discharged using an air push-type stick-like package, were very soft, and immediately broke due to physical stimulation.

Therefore, it suffices that the jelly-like composition include either ι-carrageenan or κ-carrageenan, but it is preferable that the jelly-like composition include both ι-carrageenan and κ-carrageenan.

The content of κ-carrageenan is preferably set to 0.05 to 0.6%.

The content of ι-carrageenan is preferably set to 0.01 to 0.6%.

The effect of the content of glycerol was determined.

A 32.5 mg preparation was produced in the same manner as described above according to the formulation listed in Table 3.

TABLE 3

| Component (%) | Sample | | | | | | | |
|---|---|---|---|---|---|---|---|---|
| | 11 | 12 | 13 | 14 | 15 | 16 | 17 | 18 |
| Potassium iodide | 1.625 | 1.625 | 1.625 | 1.625 | 1.625 | 1.625 | 1.625 | 1.625 |
| ι-Carrageenan | 0.5 | 0.5 | 0.5 | 0.5 | 0.5 | 0.5 | 0.5 | 0.5 |
| κ-Carrageenan | 0.11 | 0.11 | 0.11 | 0.11 | 0.11 | 0.11 | 0.11 | 0.11 |
| Carob bean gum | 0.19 | 0.19 | 0.19 | 0.19 | 0.19 | 0.19 | 0.19 | 0.19 |
| Sodium polyacrylate | 0.003 | 0.003 | 0.003 | 0.003 | 0.003 | 0.003 | 0.003 | 0.003 |
| Glycerol | 10 | 5 | 20 | 15 | 13 | 17 | 0 | 7 |
| D-Sorbitol | 20 | 20 | 20 | 20 | 20 | 20 | 20 | 20 |
| Sodium saccharin | 0.2 | 0.2 | 0.2 | 0.2 | 0.2 | 0.2 | 0.2 | 0.2 |
| Sodium citrate hydrate | 0.5 | 0.5 | 0.5 | 0.5 | 0.5 | 0.5 | 0.5 | 0.5 |
| Citric acid hydrate | 0.03 | 0.03 | 0.03 | 0.03 | 0.03 | 0.03 | 0.03 | 0.03 |
| Propylparaben | 0.015 | 0.015 | 0.015 | 0.015 | 0.015 | 0.015 | 0.015 | 0.015 |
| Flavor | 0.1 | 0.1 | 0.1 | 0.1 | 0.1 | 0.1 | 0.1 | 0.1 |
| Purified water | Proper quantity | Proper quantity | Proper quantity | Proper quantity | Proper quantity | Proper quantity | Proper quantity | Proper quantity |
| Total | 100 | 100 | 100 | 100 | 100 | 100 | 100 | 100 |

When glycerol was not added (Sample No. 17), the resulting preparation was in the form of jelly, but was very soft, and was not suitable for an air push-type application.

Sample No. 13, which had a glycerol content of 20%, was solidified in the form of jelly in a state in which bubbles remained.

Therefore, the content of glycerol is preferably set to 3 to 20%, more preferably 5 to 17%, and still more preferably 7 to 15%.

Figure 8:
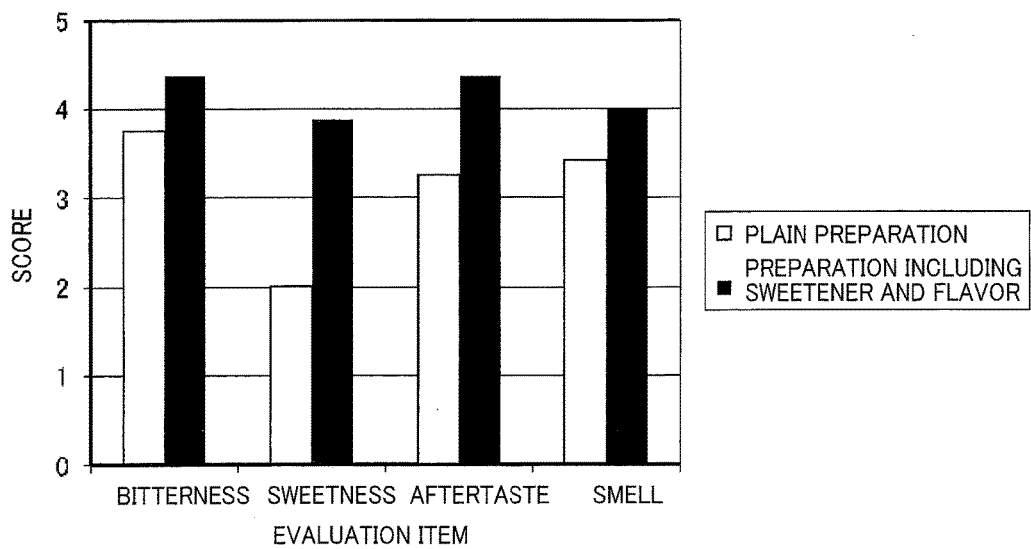
FIG. 8 illustrates results of a questionnaire with regard to ease of intake.

FIG. 8 illustrates the results of a questionnaire with regard to ease of intake depending on the presence or absence of the sweetener and the flavor (strawberry flavor).

FIG. 8 illustrates the results of a comparison between a plain preparation that did not include sodium saccharin and a flavor and the 16.3 mg preparation according to the invention.

It was confirmed from the results illustrated in FIG. 8 that the jelly-like pharmaceutical composition according to the invention can be taken easily.

A formulation that can produce a jelly that can be easily discharged using an air push-type stick-like package, and is as soft as (or softer than) baby food was determined in view of the intended use (target age group) of the preparation.

Sample No. 10 in which the ratio (content) of κ-carrageenan was 0.3% and the ratio (content) of ι-carrageenan was 0% immediately broke due to physical stimulation. Therefore, a small amount of ι-carrageenan was added while setting the ratio of κ-carrageenan to 0.3% or less.

The formulation is listed in Table 4.

TABLE 4

| Component (%) | Sample | | | |
|---|---|---|---|---|
| | 19 | 20 | 21 | 22 |
| Potassium iodide | 1.625 | 1.625 | 1.625 | 1.625 |
| ι-Carrageenan | 0.03 | 0.01 | 0.02 | 0.05 |
| κ-Carrageenan | 0.2 | 0.2 | 0.2 | 0.3 |
| Carob bean gum | 0.13 | 0.13 | 0.13 | 0.19 |
| Sodium polyacrylate | 0.003 | 0.003 | 0.003 | 0.003 |
| Glycerol | 10 | 10 | 10 | 10 |
| D-Sorbitol | 20 | 20 | 20 | 20 |
| Sodium saccharin | 0.2 | 0.2 | 0.2 | 0.2 |
| Sodium citrate hydrate | 0.5 | 0.5 | 0.5 | 0.5 |
| Citric acid hydrate | 0.03 | 0.03 | 0.03 | 0.03 |
| Propylparaben | 0.015 | 0.015 | 0.015 | 0.015 |
| Purified water | Proper quantity | Proper quantity | Proper quantity | Proper quantity |
| Total | 100 | 100 | 100 | 100 |

In Table 4, the unit for the ratio (content) of each component is "mass %".

In Samples No. 19 to No. 22, the ratio (content) of carob bean gum was adjusted corresponding to the ratio (content) of κ-carrageenan (i.e., κ-carrageenan:carob bean gum=6:4).

The softness of Samples No. 19 to No. 22 listed in Table 4 was compared with that of commercially-available baby food.

Measurement of Softness

The softness ($N/m^2$) was measured using a rheometer ("CR-500DX" manufactured by Sun Scientific Co., Ltd.).

Specifically, the sample was put in a container having a diameter of 40 mm up to a height of 15 mm, and the softness was measured using a plunger having a diameter of 20 mm at a compression rate of 10 mm/sec and a clearance of 5 mm.

The softness of commercially-available baby food "Uragoshi Ringo" was 465.0 $N/m^2$, the softness of commercially-available baby food "Tomato & Fruits Dessert" was 659.2 $N/m^2$, the softness of Sample No. 19 was 353.5 $N/m^2$, the softness of Sample No. 20 was 331.2 $N/m^2$, the softness of Sample No. 21 was 340.8 $N/m^2$, and the softness of Sample No. 22 was 455.4 $N/m^2$.

Specifically, Samples No. 19 to No. 22 were softer than the commercially-available baby food.

Note that it is considered that softness of 500 $N/m^2$ or less is required to swallow food.

Measurement of Spread Due to Fall 2 g of each of Samples No. 19 to No. 22 and commercially-available baby food "Tomato & Fruits Dessert" was put in an air push-type stick-like package, and discharged vertically at a height of 25 cm (allowed to fall) to measure the spread area.

The spread area of the commercially-available baby food was 406 $mm^2$, the spread area of Sample No. 19 was 351 $mm^2$, the spread area of Sample No. 20 was 372 $mm^2$, the spread area of Sample No. 21 was 359 $mm^2$, and the spread area of Sample No. 22 was 349 $mm^2$. Specifically, the spread area of Samples No. 19 to No. 22 was close to that of the commercially-available baby food.

It was thus confirmed that Samples No. 19 to No. 22 had softness almost equal to that of the commercially-available baby food.

Production Scale and Stirring Conditions

Samples No. 19 to No. 22 were produced on a laboratory scale, and the stirring operation was performed using a stirring bar.

Since a large-scale commercial production process utilizes equipment provided with a high-speed stirrer, it is considered that the state of the resulting product is affected by the production scale and the stirring mechanism.

Therefore, a product having the same formulation as that of Sample No. 19 and a product having the same formulation as that of Sample No. 22 were produced on a large scale using equipment provided with a high-speed stirrer, and the softness of each product was measured.

The softness of the product having the same formulation as that of Sample No. 19 was 261 $N/m^2$, and the softness of the product having the same formulation as that of Sample No. 22 was 274 $N/m^2$ (i.e., an improvement in softness was observed with respect to Samples No. 19 and No. 22).

CONCLUSION

It was confirmed from the evaluation results that a jelly-like preparation having softness close to that of baby food can be obtained by setting the ratio (content) of κ-carrageenan to 0.1 to 0.5%, and setting the ratio (content) of ι-carrageenan to 0.01 to 0.08%.

INDUSTRIAL APPLICABILITY

The iodine preparation according to the invention is in the form of jelly, and can be adjusted in softness corresponding the target age group (e.g., newborn baby or infant).

What is claimed is:

1. A jellied oral pharmaceutical composition comprising potassium iodide as an active ingredient, a gelling agent, a dispersion medium, and a sweetener,
    wherein the gelling agent comprises 0.01 to 0.08% of ι-carrageenan and 0.1 to 0.3% of κ-carrageenan,
    the dispersion medium is a mixture of water and 7 to 15% glycerin, and
    the sweetener comprises 15 to 25% of D-sorbitol,
    wherein the jellied oral pharmaceutical composition is disposed in a stick package, the stick package containing the jellied oral pharmaceutical composition and air.

2. The jellied oral pharmaceutical composition as defined in claim 1, wherein the gelling agent is further combined with a carob bean gum at a κ-carrageenan:carob bean gum ratio of 6:4.

3. The jellied oral pharmaceutical composition as defined in claim 1, further comprising a stabilizer, wherein the stabilizer comprises any one selected from the group consisting of polyacrylic acid, partially neutralized polyacrylic acid, and a polyacrylic acid salt.

4. The jellied oral pharmaceutical composition as defined in claim 1, further comprising at least one selected from the group consisting of a buffer, a preservative, and a flavor.

5. The jellied oral pharmaceutical composition as defined in claim 1, wherein the gelling agent comprises 0.01 to 0.05% of ι-carrageenan and 0.2 to 0.3% of κ-carrageenan.

\* \* \* \* \*